United States Patent [19]

Brisson et al.

[11] Patent Number: 4,763,652
[45] Date of Patent: Aug. 16, 1988

[54] AIMING SYSTEM FOR KIDNEY STONE DISINTEGRATOR

[75] Inventors: Alfred G. Brisson, Kildeer; Christopher Nowacki, Arlington Heights, both of Ill.; William R. Shene, Plattsburgh, N.Y.; Thomas H. Burdick, Deerfield; Exequiel Dela-Cruz, Arlington Heights, both of Ill.

[73] Assignee: Northgate Research, Inc., Arlington Heights, Ill.

[21] Appl. No.: 852,835

[22] Filed: Apr. 16, 1986

[51] Int. Cl.⁴ .............................................. A61B 17/22
[52] U.S. Cl. .................................. 128/328; 128/24 A
[58] Field of Search .............................. 128/328, 24 A

[56] References Cited

U.S. PATENT DOCUMENTS

| | | | |
|---|---|---|---|
| 3,735,755 | 5/1973 | Eggleton et al. | 128/303 R X |
| 3,942,531 | 3/1976 | Hoff et al. | 128/328 |
| 4,230,129 | 10/1980 | Le Veen | 128/804 |
| 4,311,147 | 1/1982 | Hausler | 128/328 |
| 4,539,989 | 9/1985 | Forssmann et al. | 128/328 |
| 4,543,959 | 10/1985 | Sepponen | 128/660 X |
| 4,617,931 | 10/1986 | Dory | 128/328 |
| 4,620,546 | 11/1986 | Aida et al. | 128/24 A X |
| 4,669,483 | 6/1987 | Hepp et al. | 128/660 |

OTHER PUBLICATIONS

"Contact-free Destruction of Kidney Stones by Extracorporeally Produced, Focused Shock Waves"—C. Chaussy, B. Forssmann, W. Brendel, D. Jocham, F. Eisenberger, W. Hepp, J. M. Gokel, 56 Illustrations and 8 Tables, 1980.
"Shock Wave Treatment for Stones in the Upper Urinary Tract", Christian Chaussy, M.D. and Egbert Schmiedt, M.D., Urologic Clinics of N. America, vol. 10, No. 4, Nov. 1983, *Symposium on Surgery of Stone Disease*.

Primary Examiner—Michael H. Thaler
Attorney, Agent, or Firm—Robert M. Wolters

[57] ABSTRACT

A kidney stone disintegrating system includes a computer-controlled aiming system. The disintegrating system includes a reflector containing water through which the reflector is coupled to a living body having a kidney stone. The reflector is a portion of an ellipsoid and a spark gap generator is located at one focus of the ellipsoid. An electrical energy source is connected to the spark gap generator for generating a spark which in turn generates a shock wave in the fluid. Three motors are connected to the reflector for moving it in respectively X-axis, Y-axis and Z-axis directions to locate the reflector so that the kidney stone lies at the second focus point thereof. A pair of ultrasound transducers are carried by an articulated support comprising a plurality of pivotally interconnected arms. Precision potentiometers are provided between the arms to indicate the relative positions thereof, and electrical potentials from the potentiometers are connected to a computer. The signals and the computer are connected to a monitor having a screen to display the kidney stone, and particularly the position thereof as determined by the two transducers. The computer is connected to the three motors to position the reflector in accordance with the positions of the transducers to locate the reflector with the second focus point coinciding with the kidney stone. Controls are provided for causing generation of a spark with the resulting shock wave focused on the kidney stone to destroy the kidney stone.

6 Claims, 2 Drawing Sheets

AIMING SYSTEM FOR KIDNEY STONE DISINTEGRATOR

BACKGROUND OF THE INVENTION

Kidney stones, and also naturally-occurring stones in the bladder and the ureter can be exquisitely painful, and often require surgical relief. Excision or destruction of stones in the bladder and sometimes in the ureter can be relatively easily accomplished, but removal of stones from the kidney is a major procedure.

Removal of stones from the kidney is a very serious and traumatic procedure. A large incision is made in the body. The kidney is essentially removed from the body and cut open. The stone or stones are then removed, whereupon the kidney is sutured and returned to the body, with the body then being sutured. Typical recovery time is on the order of six months.

Chemotherapy is available as a non-invasive therapy for uric acid stones. In this therapy the urine is alkalized. The existing stone thus is dissolved over a substantial period of time, and in most cases the patient can be cured before his condition becomes acute. However, the patient's condition is often already acute when the stone is discovered, and immediate surgery is imperative. Attempts at chemical dissolution of other types of stones have not been successful.

There are procedures for removing stones from the bladder which do not require cutting of the body. The first known of these is an invasive procedure in that the necessary device is inserted through the urethra. A correlary approach to ureteral and kidney stone disintegration is known as the percutaneous approach. A needle is inserted through the skin to the renal pelvis, the collecting area of the kidney. The needle is hollow and a guide wire is inserted through the needle into the kidney. The needle is then removed, and successively larger tubes are run in over the guide wire, leaving a fine tube 8 mm in diameter. Viewing and stone cracking apparatus then are inserted through this tube to crack or disintegrate the stone. The approach is still invasive and traumatic to the patient.

In both the percutaneous approach and the insertion through the urethra, an electrohydraulic impulse is provided. A high energy capacitor is discharged establishing a hydrodynamic wave which destroys the concretion upon contact. In either of these approaches the electrode must be in close proximity to the stone, and a cystoscope having an optical telescope is utilized to visualize the spark-generating electrodes.

Ultrasonic waves on the order of 27 KHz are used as an alternative technique to disintegrate bladder stones. An optical device and an ultrasound converter are carried by a hollow steel probe which is inserted through the urethra. High frequency electrical energy is transformed into mechanical energy by an ultrasound converter and carried by a hollow steel probe which must be in contact with the bladder stone.

With both electrohydraulic impulses and ultrasonic disintegration of bladder stones it was initially necessary for the energy source to be very close to or to effect physical contact with the stone. Although this did require invasion of the body, major cutting of the body was not necessary.

One approach has been made to the non-invasive breaking up or disintegration of kidney stones in the body as disclosed in U.S. Pat. Nos. 3,942,531 Hoff et al and 4,311,147 Hausler. The first of these patents is exemplified in a machine commerically available in the Federal Republic of Germany from Dornier System GmbH. A few of the Dornier machines are now in use in the United States. Such machines are quite large since they require the patient to be immersed in a tub of water in a crouched, face-up position. Two dimensional X-ray procedures are utilized to determine the position of the stone by moving the patient. The machine includes an underwater spark gap shock wave generator which lies outside of the patient's body and at the first focus point of an ellipsoidal reflector. The patient is moved around in the water bath by several mechanisms utilizing a two-dimensional X-ray technique until the kidney stone is positioned at the second focal point of the ellipsoid. Since X-rays are used only radio opaque stones can be located. The shock wave is then generated, and passes through the water bath and through the patient's body to convey the energy to the kidney stone. The kidney machine requires a 40 square meter room 3 meters in height. The machine base is 6 meters by 1 meter. The cost of such a machine, which may be expected to rise with inflation, is on the order of 2 million dollars, plus ten percent of the price of the machine each year for a service contract. The service contract includes the cost of the technician who must be on hand at all times when the machine is in operation. It is contraindicated if the ureter is blocked, since the material must pass out through the ureter. It is also unsuccessful with radio transparent or translucent stones, since they cannot be located by X-ray techniques. It must be emphasized that precise aiming of an external shock wave is necessary since energy focused into an air or gas pocket in the body can cause damage to interface tissue.

Efforts have been made to produce a physically smaller machine which does not require immersion of the body of the patient in a tub of water. One patent showing such an effort is Forssmann, U.S. Pat. No. 4,539,989. The structure in this Patent utilizes an ellipsoidal reflector coupled to the body through a liquid-filled cushion and having an energy absorber and reflector on the back side of the body. A three-dimensional X-ray aiming technique again is used.

Efforts have been made to utilize ultrasound techniques for aiming, see for example the co-pending patent application of William R. Shene, Christopher Nowacki, and Alfred G. Brisson, Ser. No. 666,770, filed Oct. 31, 1984 for "KIDNEY STONE DISINTEGRATOR". An earlier effort at ultrasound aiming which was abandoned in favor of X-ray aiming is found in Chaussy, "Extracorporeal Shock Wave Lithotripsy", Beruhrungsfreie Nierensteinzertrummerung durch extrakorporeal erzeugt, fokussierte Strosswellen", Beitrage zur Urologie, vol. 2 (Karger, Basel, 1980), ISBN 3-8055-1901-X Translation Copyright 1982 by S. Karger AG, P. O. BOX, CH-4009 Basel, Switzerland. Printed in Germany by Ernst Kieser GmbH, D-8900 Augsburg ISBN 3-8055-3620-8,128/328 pages 1–112, see especially pages 38 and 39 and FIG. 21. In accordance with the Chaussy disclosure, the ultrasonic transducers were fixed in the structure of the ellipsoidal reflector and operated through the water bath coupling the spark gap to the body containing the kidney stones. It appears that Chaussy abandoned attempts at ultrasonic aiming in favor of X-ray aiming.

OBJECTS AND SUMMARY OF THE PRESENT INVENTION

It is an object of the present invention to provide an aiming system for an extracorporeal kidney stone destruction system which utilizes three dimensional ultrasonic aiming connected through a computer to mechanism for moving an ellipsoidal reflector to position it so that the kidney stone to be destroyed is at the second focal point of the reflector, a shock wave generating spark gap being at the first focal point.

The aiming system of the present invention utilizes an ultrasonic imaging technique. This technique uses focused ultrasonic energy in the reflectance mode to provide the information used to construct the image. The reflectance mode means that the ultrasonic energy is sent out from and reflected back to the same transducer or two transducers located in close proximity to each other. This ultrasonic energy is transmitted in the form of a very short pulse ($T<3$ uS) of a specified frequency. This pulse of energy travels out from the transducer into the tissue. When the ultrasonic energy comes in contact with the boundry between two substances with different acoustic impedances a portion of the ultrasonic energy is reflected back in the direction of the original pulse. This energy is detected when it reaches the transducer and the time it takes the energy to go out and return is determined. Since the speed of ultrasound in tissue is relatively constant the distance to the reflecting surface can be determined. The portion of the energy not reflected at this boundry continues on and parts of this remaining energy will be reflected back at deeper tissue interfaces. This technique gives all of the information required i.e. direction and distance, to construct a picture of the tissue in the plane of the ultrasound travel.

The aiming system used in the machine built by the Dornier company in West Germany is based on the use of X-ray rather than ultrasound. X-ray equipment operates in the transmittance rather than the reflectance mode. This means that the X-ray generator is placed on one side of the patient and the detector is placed on the other side of the patient. The X-rays are transmitted through the patient and part of the X-ray energy is absorbed by the tissue. Different types of tissue absorb X-ray energy in different amounts. Therefore the amount of energy arriving at the detector is dependent on the type of tissue between the generator and detector. This information is adequate to construct a plain view image. However, because it operates in the transmittance mode, no depth information is available. Therefore, to obtain precise information of the location of a calculus in three dimensions, two X-ray systems located in the same plane at ninety degree angles to each other must be used. This is the technique used in the Dornier machine. X-ray radiation aiming works only with radio opaque calculi. Stones that are transparent or translucent cannot be located.

Both the ultrasound and X-ray techniques have their own advantages and disadvantages. The major advantage of the X-ray technique is that it provides very accurate information that is rather easy to interpret. The image of the calculus is visible in both X-ray monitors and one need only align the patient so that the calculus is in the proper position on both screens and the aiming of the shock wave is complete. The disadvantage of the X-ray aiming technique is that the equipment is very large and very expensive. This means that a machine like the Dornier unit that uses the X-ray techniques requires a dedicated room in the hospital and it is a major project to install and to maintain the machine. The expense of the machine is also so great that it limits the machine to either major hospitals or stone treatment centers. A second disadvantage of the X-ray technique is that it exposes the patient to repeated doses of ionizing radiation which is known to be harmful. The operator of the machine must be isolated from the X-ray radiation. One of the advantages of the ultrasound technique is that it uses no ionizing radiation and is therefore safer for the patient. Another advantage of the ultrasound technique is that the equipment is far less expensive, smaller, and easier to maintain. Therefore a machine built around the ultrasound aiming technique is smaller, less expensive to purchase, and less expensive to maintain than the Dornier unit. The major disadvantage of the ultrasound aiming technique is that the image is not as clear or nearly as easy to interpret as the X-ray image. This is especially true in the case of calculus because they do not image well when using ultrasound. Therefore for ultrasound to be a practical imaging method for this type of machine a technique must be developed to make the image easier to interpret.

As stated above. when ultrasonic energy traveling through the body encounters a boundry between two tissues of differing acoustic impedance a portion of that energy is reflected back to the transmitting source and the remaining portion of the energy continues on deeper into the body. The amount of energy reflected back is directly proportional to the difference between the acoustic impedance of the substances at the boundry. The acoustic impedance of a renal stone is very different from the acoustic impedance of the surrounding tissue. Also the stone presents two boundaries one as the energy enters the stone and a second as the energy leaves the stone. Since the portion of the energy that is reflected is proportional to the differences in acoustic impedances a very large portion of the energy is reflected at the tissue stone boundry. This means that very little energy passes out into the tissue behind the stone and therefore no echoes return from behind the stone. This causes a shadow to appear behind the stone on the B-scan image, and noting this shadow is one of the easiest ways to find the location of a stone. The stone will be on a direct line drawn through the shadow in the direction of the transmitting and receiving transducer. Therefore, although the stone does not produce an excellent image in itself, its presence can be shown by the acoustic shadow that it causes.

In order to produce an acoustic shadow behind the stone a B-scan image is required. A B-scan image is an image that shows position on the X-axis versus depth into the body on the Y-axis. Two of the more popular techniques used to produce a B-scan are the Linear scan and the Sector scan. The Linear scan uses a series of transducers arranged in a linear array and each transducer is pulsed in sequence. The result is an image that is a rectangular shape with one side representing distance and the other side representing depth into the body. The Sector scan uses a single transducer array where the beam is electronically steered in a sweeping motion from a single point of origin. The image produced is in the shape of a slice out of a pie with the depth into the body shown by distance from the point of origin. For our purpose the Sector scan is the choice. This is due to the size and shape of the transducer.

One of the advances in imaging technology is a digital image enhancement technique known as a compound image. This technique has been made possible on a large scale basis by the advancements in microcomputers and solid state digital memories. Until recently the cost of this equipment would have made this technique cost prohibitive for the present invention. The compound B-scan image is produced by combining two or more individual B-scan images of the same area of the body. Each of the individual images is taken from a different location on the body which gives several views of the same area from different angles. These views are then combined into one image that retains certain qualities of each individual image. The qualities of each individual image that are either retained or not retained are determined by the mathematical process that is used to combine the individual images into a single image.

To create a compound B-scan image each individual image must be broken down into a matrix of points. Each point in the matrix represents a point of light on the image. The number of points in the matrix determines the resolution of the final image. A typical matrix would consist of 256 points in the X-axis and 256 points in the Y-axis. This means that each individual B-scan image consists of 65,536 points of light. Each of these points of light is represented by a number stored at a location in a digital microcomputer memory. The value of each number gives the brightness of each location in the image. To combine a number of these individual B-scan images into one image each pixel location or point of light on each image must be examined by the computer and the numerical value of each of these locations in each of the images must be used to determine the value for each pixel location in the final image. The mathematical process used to combine these images will have a tremendous effect on the information conveyed by the final image. Three popular combination processes are:

1. Peak

In this technique the computer checks each pixel position in each individual image and places the maximum value found into that position in the compound image.

2. Average

In this technique the computer checks each pixel position in each individual image and places the average of the values found in the individual images into that position in the compound image.

3. Minimum

In this technique the computer checks each pixel position in each individual image and places the minimum value found into that position in the compound image.

The minimum detection technique is the best technique for the present invention. This is because any acoustic shadow that is present in any of the individual B-scan images will be preserved in the final compound image. Because each of the individual images was made from a different transducer location the acoustic shadow produced by a stone will be at a different angle in each image. When all of the images are combined into one image using the minimum detection technique all of the shadows will be present but each will be at a different angle. When a line is drawn through the length of each of the shadows it will pass through the center of the stone. If a line is drawn through two or more shadows on a compound image the point on the image where the lines intersect will be the center of the stone. Therefore this method allows the location of the center of the stone to be accurately determined even though the shape of the stone is not visible on the image.

The vast majority of the effort required to implement the technique described above on a day to day basis in the clinical environment is handled by the computer that is built into the machine. Once the machine is connected to the patient the computer automatically obtains a B-scan from each transducer and combines these images to form the final scan.

This compound scan is analyzed by the computer and if a shadow pattern is found it draws the lines through each of the shadows and superimposes these lines over the scan. The operator can see the intersection of the lines superimposed over the B-scan image and he or she will make the final determination if the destruction of a stone should be attempted. If no shadow pattern is found in one compound scan the transducers are moved and a second scan is made. Successive scans are made until a stone shadow pattern is found.

When a shadow pattern is recognized the computer superimposes a pattern over the compound B-scan that allows the operator to position the stone exactly in the second focal point of the ellipsoidal reflector. The operator sees a crosshair type display. He or she then uses a set of switches to instruct the computer to move the reflector until the center of the crosshair display is directly over the intersection of the lines drawn through the shadows. Because the computer knows the exact positions of the transducers and the reflector this will position the stone directly in the second focal point of the reflector.

The actual firing of the machine is initiated by the operator. The computer monitors the ECG of the patient, the status of the energy generator, the position of the reflector, and the operator controls. When the operator initiates the firing the computer checks all machine parameters and if all are within limits the computer causes the energy generator to fire in synchronization with the R-wave of the patients ECG. The machine continues to fire until the specified number of shots has been delivered. The operator has the capability to stop the procedure at any time.

THE DRAWINGS

FIG. 1 is a perspective view somewhat stylized showing the present invention apparatus as used by a doctor or technician on a patient and FIG. 2 is a block diagram of the invention.

DETAILED DESCRIPTION OF THE ILLUSTRATED EMBODIMENT

Figure 1:
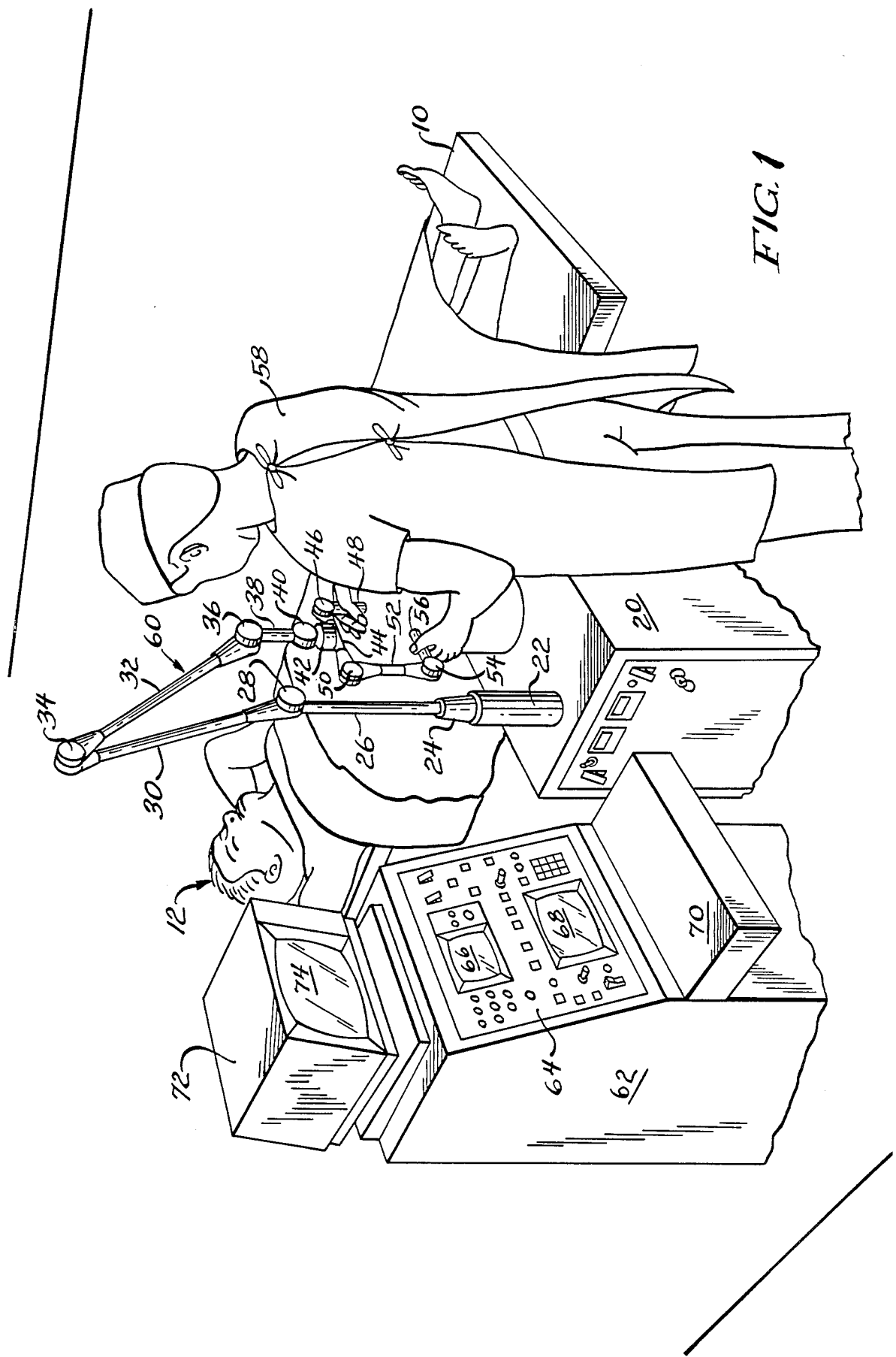

As may be seen in FIG. 1 the present invention includes a table 10 on which a patient 12 lies on his back. The patient has previously been diagnosed as having one or more calculi such as kidney stones or stones in the upper ureter. The patient lies on his back on the table 10, and a portion of the table is relieved or cut away to expose the area of the patient's back immediately adjacent to the kidneys. The approach to the back is preferred as giving a relatively unobstructed approach to both kidneys. A reflector 14 (FIG. 2) is positioned within the cut out area of the table for engagement with the patient's back. The reflector is filled with water which engages with the patient's back either directly or through a diaphragm. The reflector is movable, as will be brought out in greater detail hereinafter, and is ellipsoidal. An ellipsoid is important in that it is a rotational geometric figure having two focus points. A spark gap generator 16 is positioned at the first focus point, and the reflector 14 is moved relative to the patient 12 so that the calculus or kidney stone 18 lies at the second focus point of the ellipsoidal reflector. Discharge of an electrical capacitor through the spark gap generator 16 causes vaporization of a certain quantity of water and corresponding development of a shock wave. The shock wave travels, partly directly and partly by reflection from the walls of the reflector to the kidney stone 18 through the water in the reflector and through the tissues of the patient's body. Aiming is critical, not only to insure that the kidney stone is at the second focus point where it will be subjected to the shock wave, but in that the shock wave can be injurious to the body of the patient if the second focus point is in an improper area of the patient's body, for example within an area filled with gas.

A base 20 is disposed immediately adjacent to the table 10 and is fixed relative thereto. The base 20 is provided with an upwardly extending cylinder 22 fixed thereon and having a sleeve 24 rotatably received therein. A sending device is incorporated between the cylinder 22 and the sleeve 24 to indicate the relative rotational position of the sleeve relative to the cylinder, the latter being fixed relative to the base. The sending device in a preferred example comprises a precise analog potentiometer which produces an analog voltage related to the position of the sleeve 24 relative to the cylinder 22. It is contemplated that a digital type resolver could be used, but there are many pivotal joints to be monitored as will be apparent hereinafter. If a digital type resolver is used, then there must be 12 wires out of each resolver, and a multiplexing system preferably would be used. This results in a considerably more complicated structure, although eliminating the noise problem inherent in analog devices.

Figure 2:
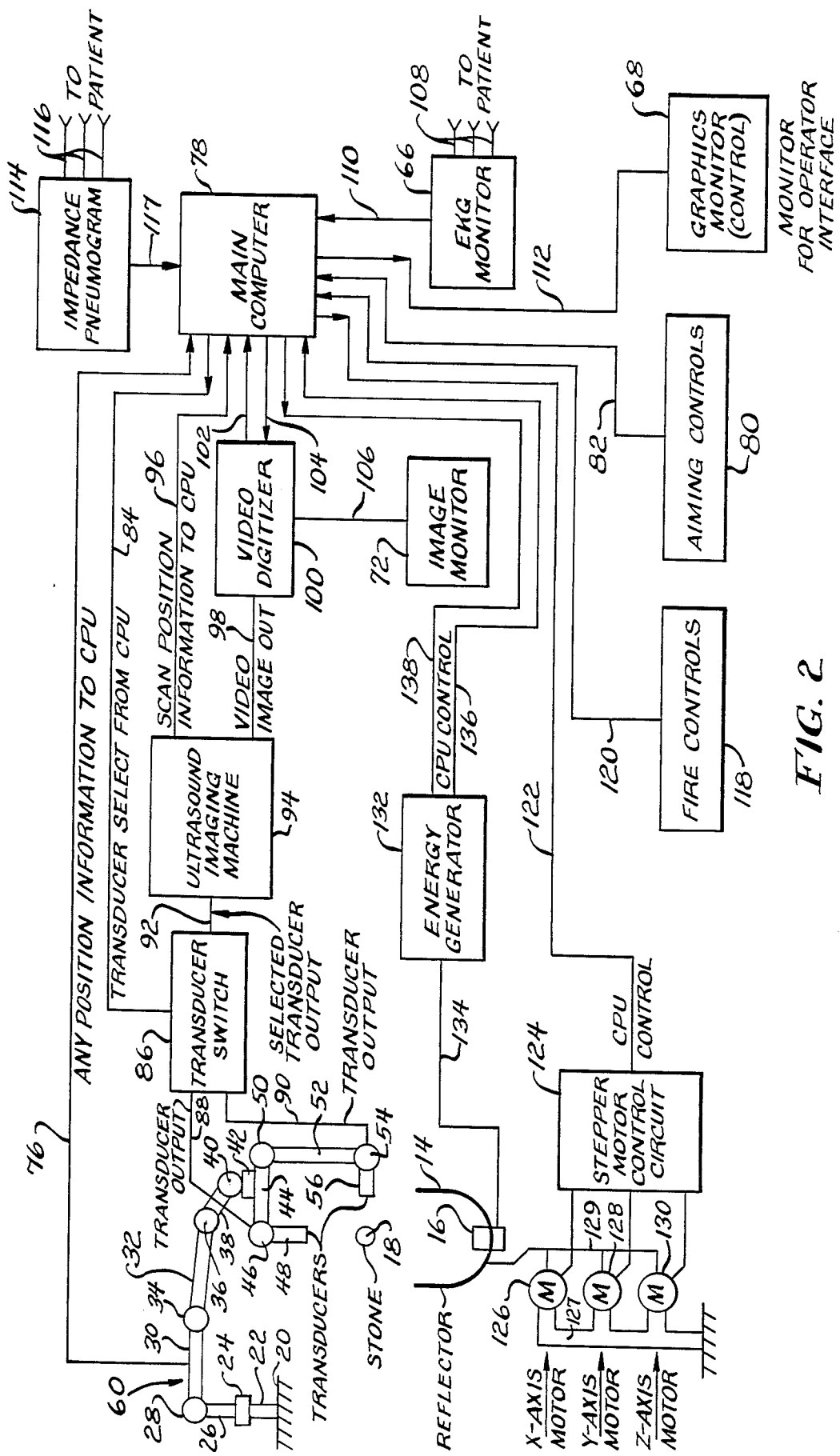

An arm or shaft 26 extends straight up from the sleeve 24 in which it is fixed. At the upper end of the arm 26 there is another pivoted joint or articulation 28 joining a shaft or arm 30 to the arm 26, and allowing pivoting about the horizontal axis. The pivotal structure 28 again preferably incorporates a precise analog potentiometer. Both arms 26 and 30 are elongated, and a further elongated arm 32 is pivotally connected to the arm 30 by means of another precise analog potentiometer joint 34, again permitting pivoting about a horizontal axis. As shown in FIGS. 1 and 2 the arms 26 and 30 extend upwardly, while the arm 32 extends downardly. At the lower end of the arm 32 there is another pivotal connection 36 including a precise analog potentiometer and pivotally connecting a relatively short arm 38 to the elongated arm 32. The joint 36 permits pivoting about a horizontal axis. At the lower end of the short arm 38 there is a pivot joint 40 for effecting pivoting about a horizontal axis, to which is connected a pivot joint 42 for effecting pivoting about a vertical axis. The joints 40 and 42 both incorporate precise analog potentiometers.

The pivot joint 42 is connected substantially midway of a relatively short, generally horizontal arm 44. At one end of the arm 44 (the right end in FIG. 1) a pivotal joint 46 permitting pivoting about a horizontal axis carries an ultrasound transducer 48. This transducer includes both a sending device and a pick-up device. At the opposite end of the arm 44 there is another pivotal joint 50 permitting pivoting about a horizontal axis, and supporting a relatively short vertical arm 52, having at its lower end a pivot joint 54, again permitting pivoting about a horizontal axis. The pivot joint 54 mounts an ultrasonic transducer 56 similar to the ultrasound transducer 48, both of the transducers 48 and 56 lying in a common plane. The pivot joints 46, 50 and 54 again incorporate precise analog potentiometers, just as all of the previously-mentioned joints.

The ultrasound transducers 48 and 56 are manually movable by a person 58 who may be a doctor, a nurse or a technician. The transducers remain in their common plane, but are movable up and down and sideways, and also may be swiveled due to the articulation of the support structure for the transducers, which support structure is hereinafter identified generally by the numeral 60. The various precise analog potentiometers provide analog information which in aggregate indicates exactly the positions of the ultrasound transducers 48 and 56. This information is used to position the reflector 14 as will be described more extensively hereinafter in connection with FIG. 2 and the balance of FIG. 1.

An electronic control unit 62 is mounted on the floor near the table 10 and support 20 and has an upwardly inclined control face 64 having various control members and indicator lights mounted thereon, and also having an EKG (electrocardiogram) video display screen 66 and a graphics display screen 68. A subjacent table surface 70 provides space for making notes, if desired. On top of the electronic control unit 62 there is mounted a monitor 72 having a video display screen 74 for displaying an image of the kidney stone that is to be destroyed.

The articulated support 60 and the transducers 48 and 54 are shown somewhat diagramitically in FIG. 2 as aimed at the kidney stone 18. Position information from the various precise analog potentiometers is fed by way of a conductor 76 to a main computer or CPU 78. Various aiming controls 80 are connected by conductor means 82 to the main computer 78, and these include controls causing the computer to act through a conductor 84 to operate a transducer switch 86. The transducer 48 is connected by a transducer output conductor 88 to the transducer switch, and the transducer 56 is connected by way of a transducer output connector 90 to the transducer switch. One or the other transducer, as determined by the CPU through the conductor 84, is connected at 92 to an ultrasound imaging machine 94. This machine provides scan position information to the CPU over conductor means 96, and also provides a video image out signal on a conductor 98 to a video digitizer 100. The video digitizer also provides a signal on a line or conductor 102 to the CPU 78, and the latter provides a signal back on a conductor 104 to the video digitizer. An output from the video digitizer is connected by a conductor 106 to the image monitor 72 to provide a computer enhanced image of the kidney stone on the video display screen 74 for observation by the operator 58.

The EKG monitor 66 previously referred to is connected by suitable wires 108 to the patient. The particular connections are not specifically shown since these may be any of the common electrodes universally used in the taking of an electrocardiogram. The information from the EKG monitor is connected through suitable conductor means 110 to the main computer 78. The purpose for this is that for patients' safety, the shock wave for destroying the kidney stone is applied only during a particular part of the cardiac wave to insure against damage to the heart or possibly induced fibrillation thereof.

The computer 78 is connected through suitable conductor means 112 to the graphics monitor for allowing the operator 58 to view various operating parameters. An impedance pneumogram apparatus 114 is provided which is connected to the patient as shown schematically by lines 116. The impedance pneumogram apparatus develops a pneumogram which is fed to the computer at 117. The purpose for this is that the position of the kidney stone changes relative to the supporting table as the patient breathes. The total process of disintegrating a kidney stone takes on the order of one hour, and it is obviously impossible for the patient to hold his breath for the entire time, or even for selected periods of time during the hour. As a result, information as to the change in position of the kidney stone with breathing is fed into the computer, and this causes constant correction of the position of the reflector 14 beneath the patient, whereby always to keep the stone 18 at the second focus point of the reflector.

Fire controls 118 which may include a manual start push-button, a selector for the number of pulses to be delivered and a stop button are connected through conductor means 120 to the computer 78.

The computer 78 is connected through a line or suitable conductor means 122 to a stepper motor control circuit 124. The stepper motor control circuit is individually connected to three stepper motors 126, 128 and 130, respectively comprising an X-axis motor, a Y-axis motor and a Z-axis motor. The motors are all in predetermined fixed positions as determined by a support 127 which is fixed relative to the floor, and hence relative to the table 10 and the support 20. The motors are connected through individual linkages to a common linkage 129 connected to the reflector 14 for controlling the position of the reflector as determined by the computer 78.

An energy generator 132 comprises essentially a voltage source and a capacitor which charges, and then is discharged through a conductor 134 to the spark gap 16 to generate a spark under water, causing vaporization of water and development of a shock wave at the first focus point of the reflector, which energy is concentrated on the kidney stone at the second focus point to effect disintegration of the kidney stone. The condition of the energy generator, and particularly the charge on the capacitor is connected through a line 136 back to the computer 78, and another line 138 connects the computer to the energy generator to control firing thereof as determined by the computer.

In operation of the apparatus as heretofore shown and described, the ultrasound transducers 48 and 56 are moved manually in their common plane. It is simple to approach from the top as illustrated herein, but is equally possible to approach from beneath the patient, or from the side thereof. Similarly, although two ultrasound transducers have been illustrated, it is possible to operate with one ultrasound transducer sequentially positioned in either of two right-angle, common-plane positions with the images from the transducer being fed sequentially into the main computer 78. In any event, the image information from the transducers is selectively supplied by way of the transducer switch 86 to the ultrasound imaging machine 94, and ultimately to the image monitor 72. The operator 58 can observe the image and can "zero in" on the kidney stone 18. Information from the ultrasound imaging machine 94 and from the video digitizer 100 is provided to the main computer 78, which in turn acts through the conductor means 122 and stepper motor control circuit 124 and the respective motors 126, 128 and 130 to position the reflector 14 beneath the patient so that the second focus point of the ellipsoidal reflector coincides with the position of the stone 18. The impedance pneumogram developed by the apparatus 114 is fed to the computer 78, and instantaneous control over the motors 126, 128 and 130 is effected to cause the reflector to move in synchronism with the patient's breathing whereby to maintain the kidney stone at the second focus point, not withstanding the change in position of the kidney stone with the patient's breathing.

With the reflector properly positioned relative to the stone, and the stone viewed as being at the proper spot by means of the image monitor 72, the operator manipulates the fire controls 118. The fire controls include a control for determining the number of pulses that will be delivered, and also includes a push button or the like start control. The start control does not instantaneously cause firing of the energy generator 132, since the computer also processes information from the EKG monitor to ensure that firing will take place only during a particular portion of the patient's pulse pattern. The line 136 from the energy generator ensures that the computer will not try to fire the energy generator until the latter is fully charged. Thus, when the energy generator is fully charged and ready to fire, and the fire control start control has been operated, and the EKG monitor indicates the proper position in the patient's pulse pattern, the energy generator fires to discharge a spark across the gap of the spark gap apparatus 16. This causes instantaneous vaporization of the water in the reflector 114 in the vicinity of the spark gap, thus generating a shock wave at the first focal point of the reflector 14. The energy of the shock wave passes through the water and through the tissues of the patient and is focused on the second focal point which is coincident with the position of the kidney stone 18. The energy generator as it recharges will fire successive spark generating charges as determined by the number of pulses selected on the fire controls.

The operator then restudies the imaging monitor and the graphics monitor to determine the condition of the kidney stone so that treatment may be terminated when the stone has been disintegrated. It will normally take several sequences of spark generation, extending up to a period of on the order of one hour, although sometimes less. Disintegration of the kidney stone or calculus results in reduction of the stone to powder, somewhat similar to the breaking up of a piece of chalk into a powder. The powder resulting from the stone subsequently is flushed from the kidneys or urethra along with urine excreted, and this process may be speeded up by intake of more than the usual amount of fluids.

Aiming and use of the kidney stone disintegrator as now disclosed and described herein avoids the past necessity of an extended and often exquisitely painful wait on behalf of a patient to see if the stone will pass from the kidneys or ureter by itself, or at least move to a nonpainful position. It further avoids the necessity of surgery or other invasion of the human body, thereby avoiding a long convalescence and the ever present danger of infection.

The specific example of the invention as herein shown and described is for purposes of illustration only.

Various changes in structure will no doubt occur to those skilled in the art, and will be understood as forming a part of the present invention insofar as they fall within the spirit and scope of the appended claims.

What is claimed is:

1. A disintetgrating system for calculi such as kidney stones comprising a reflector, a fluid medium in said reflector coupling said reflector to a living body having calculus therein, means providing a spark gap in said reflector, electrical energy means connected to said spark gap means for generating a spark in said gap means to generate a shock wave in said fluid medium, motor means connected to said reflector for moving said reflector to focus said shock wave on said calculus, ultrasound transducer means, movable support means for said transducer means permitting manual movement of said transducer means for ultrasonically locating said calculus, electric signal means connected to said transducer means for indicating the position thereof, computer means, means electrically connecting said signal means to said computer means, means electrically connecting said computer means to said motor means to position said reflectior in accordance with the position of said transducer means to effect focusing of said shock wave on said calculus, and means for operating said electrical energy means to generate a spark in said spark gap means to produce a shock wave focused on said calculus, to disintegrate said calculus, and further including means connected to said body to develop a pneumogram thereof, and means electrically connecting said penumogram means to said computer to effect movement of said reflector to focus said shock wave on said calculus continuously with the breathing of said body.

2. A system as set forth in claim 1 wherein said motor means comprises three motors respectively connected to said reflector to move said reflector on the X-axis, on the Y-axis and the Z-axis.

3. A system as set forth in claim 2 and further including electrocardiogram means connected to said body, and electric means interconnecting said electrocardiogram means and said computer to ensure generation of a spark only during a predetermined portion of the pulse wave of said body.

4. A disintegrating system for calculi such as kidney stones comprising a reflector, a fluid medium in said reflector coupling said reflector to a living body having a calculus therein, means providing a spark gap in said reflector, electrical energy means connected to said spark gap means for generating a spark in said gap means to generate a shock wave in said fluid medium, motor means connected to said reflector for moving said reflector to focus said shock wave on said calculus, ultrasound transducer means, movable support means for said transducer means permitting manual movement of said transducer means for utlrasonically locating said caluculus, electric signal means connected to said transducer means for indicating the position thereof, computer means, means electrically connecting said signal means to said computer means, means electrically connecting said computer means to said motor means to position said reflector in accordance with the position of said transducer means to effect focusing of said shock wave on said calculus, and means for operating said electrical energy means to generate a spark in said spark gap means to produce a shock wave focused on said calculus, to disintegrate said calculus, means connecting said computer means to said energy means to effect firing thereof only when said reflector is in proper position to focus said shock wave on said calculus, and further including means connected to said body to develop a pneumogram thereof, and means electrically connecting said penumogram means to said computer to effect movement of said reflector to focus said shock wave on said calculus continuously with the breathing of said body.

5. A system as set forth in claim 4 and further including electrocardiogram means connected to said body, and electric means connecting said electrocardiogram means to said computer to effect firing of said emergy means only during a predetermined portion of the pulse wave of said body.

6. A disintegrating system for calculus such as a kidney stone comprising a reflector, a fluid medium in said reflector for coupling said reflector to a living body having a calculus therein, shock wave generating means to generate a shock wave in said reflector, electrical energy means connected to said shock wave generating means to generate a shock wave in said fluid medium, motor means connected to said reflector for moving said reflector to focus said shock wave on said calculus, ultrasound trnasducer means, movable support means for said transducer means permitting movement of said transducer means for ultrasonically locating said calculus, electric signal means connected to said transducer means for indicating the position thereof, computer means, means electrically connecting said signal means to said computer means, means electrically connecting said computer means to said motor means to position said reflector in accordance with the position of said transducer means to effect focusing of said shock wave on said calculus, means for operating said electrical energy means to produce a shock wave focused on said calculus to disintegrate said calculus, means connected to said living body to develop a pneumogram thereof, and means electrically connecting said penumogram means to said computer to effect movement of said reflector to focus said shock wave on said calculus continuously with the breathing of said body.

* * * * *